US012788391B2

(12) United States Patent
Worrel

(10) Patent No.: US 12,788,391 B2
(45) Date of Patent: Nov. 10, 2026

(54) KNOTLESS SUTURE SHUTTLING AND ANCHORING SYSTEM

(71) Applicant: SUREMKA, LLC, Dallas, TX (US)

(72) Inventor: Daniel A. Worrel, Dallas, TX (US)

(73) Assignee: SUREMKA, LLC, Dallas, TX (US)

( * ) Notice: Subject to any disclaimer, the term of this patent is extended or adjusted under 35 U.S.C. 154(b) by 227 days.

(21) Appl. No.: 18/336,287

(22) Filed: Jun. 16, 2023

(65) Prior Publication Data

US 2023/0404567 A1 Dec. 21, 2023

Related U.S. Application Data

(60) Provisional application No. 63/352,977, filed on Jun. 16, 2022.

(51) Int. Cl.
*A61B 17/04* (2006.01)
*A61B 17/06* (2006.01)

(52) U.S. Cl.
CPC .... *A61B 17/0401* (2013.01); *A61B 17/06166* (2013.01); *A61B 2017/0404* (2013.01); *A61B 2017/0414* (2013.01)

(58) Field of Classification Search
None
See application file for complete search history.

(56) References Cited

U.S. PATENT DOCUMENTS

| | | | | |
|---|---|---|---|---|
| 5,755,728 A * | 5/1998 | Maki | A61B 17/0469 606/139 |
| 9,198,656 B1 * | 12/2015 | Ferguson | A61B 17/06166 |
| 2006/0259076 A1 * | 11/2006 | Burkhart | A61B 17/06166 606/228 |
| 2008/0086147 A1 * | 4/2008 | Knapp | A61B 17/0485 606/113 |
| 2008/0312689 A1 * | 12/2008 | Denham | D04C 1/06 606/228 |
| 2009/0062854 A1 * | 3/2009 | Kaiser | A61B 17/0401 606/232 |
| 2009/0082805 A1 * | 3/2009 | Kaiser | A61B 17/06166 606/228 |
| 2009/0312776 A1 * | 12/2009 | Kaiser | A61B 17/06166 606/228 |
| 2010/0256677 A1 * | 10/2010 | Albertorio | A61F 2/0811 606/232 |
| 2011/0172701 A1 * | 7/2011 | Wales | A61B 17/0469 606/213 |

(Continued)

*Primary Examiner* — Shaun L David

(57) ABSTRACT

A knotless surgical suture system having a means for shuttling a suture having a locking limb portion having a tapering thickness for mounting to an anchor point, thereby providing a knotless anchor provided by the interference fit of the suture itself. The system can be used in conjunction with various traditional "knotted" anchors, which can be loaded with the knotless suture shuttling and anchoring system, creating a knotless fixation solution. The knotless suture shuttling and anchoring system enables a surgeon to load the sutures to the anchor and lock them in place with the tapered locking limb portion. The combination of the knotless suture shuttling and anchoring system having a shuttling limb with a suture loop allows a surgeon to load sutures onto existing anchors, with the tapered locking limb portion used to create an interference fit, locking it into place.

9 Claims, 3 Drawing Sheets

(56) References Cited

U.S. PATENT DOCUMENTS

| | | | | |
|---|---|---|---|---|
| 2011/0270278 | A1* | 11/2011 | Overes | A61B 17/0487 606/228 |
| 2012/0046693 | A1* | 2/2012 | Denham | A61B 17/06166 606/232 |
| 2013/0023928 | A1* | 1/2013 | Dreyfuss | A61B 17/06166 606/228 |
| 2013/0110165 | A1* | 5/2013 | Burkhart | A61B 17/0401 606/232 |
| 2014/0257378 | A1* | 9/2014 | Norton | A61B 17/06166 606/228 |
| 2014/0277121 | A1* | 9/2014 | Pilgeram | A61B 17/0469 57/22 |
| 2015/0066081 | A1* | 3/2015 | Martin | D04B 21/202 606/228 |
| 2015/0272567 | A1* | 10/2015 | Feezor | A61B 17/0401 606/232 |
| 2018/0021034 | A1* | 1/2018 | Ferguson | A61B 17/0485 606/228 |
| 2018/0049734 | A1* | 2/2018 | Kam | A61B 17/06166 |
| 2018/0221010 | A1* | 8/2018 | Lund | A61B 17/0401 |
| 2018/0353167 | A1* | 12/2018 | Lombardo | A61B 17/0401 |
| 2019/0365366 | A1* | 12/2019 | Petry | A61B 17/0487 |
| 2019/0380693 | A1* | 12/2019 | Burkhart | A61B 17/06166 |
| 2021/0401567 | A1* | 12/2021 | Bachmaier | A61F 2/30749 |

* cited by examiner

KNOTLESS SUTURE SHUTTLING AND ANCHORING SYSTEM

BACKGROUND OF THE INVENTION

1. Field of the Invention

The present invention relates generally to sutures, suture shuttling, and surgical fixation methods, and more specifically, to a knotless surgical suture system having a means for shuttling a suture of tapering thickness for mounting to an anchor point, thereby providing a knotless anchor provided by the interference fit of the suture itself.

2. Description of Related Art Including Information Disclosed Under 37 CFR 1.97 and 1.98

Various methods of fixation of sutures adjacent to surgical sites are known in the prior art. In fact, most tendon, labrum, and ligament repairs use some method of fixation device. Such repairs often employ anchors (for example, screw-in anchors), buttons, or "soft anchors" (for example, an all-suture anchor) which are secured to the bone, and have sutures that are looped through an eyelet in the anchor. By way of example, in surgery associated with the repair of a rotator cuff tendon tear, a hole is first formed through a bone structure adjacent to the surgical site via drilling and/or punching using a specialized elongate delivery device loaded with a suture anchor having an eyelet. Anchors are typically preloaded with sutures which are passed and tired for "knotted repair" through multiple configurations. Multiple sutures are typically then threaded through the eyelet of the anchor and secured using a suture knot. Surgeons then rely on the anchors to deliver the sutures through the tendon, and tie them down for "knotted repair." Alternatively, "knotless" anchors may be utilized, which rely on an interference fit between the suture and the bone, and are inserted into a hole that is drilled or punched. The knotless suture shuttling and anchoring system disclosed herein satisfies these needs and others as will become apparent to one of ordinary skill after a careful study of the detailed description and embodiments.

A drawback of prior art surgical fixation methods is the absence of any utilization of an interference fit of the suture itself. Such an interference fit using the suture itself would increase the variety of fixation options available to surgeons, and would further increase the flexibility of employing various manner of fixation methods and devices. In particular, an interference fit using the suture itself will provide surgeons with greater flexibility in terms of the number of sutures to be locked in, the size of sutures that can be locked in, and an ability to convert traditional anchors to knotless anchors. An interference fit using the suture itself will also provide surgeons with the ability to make suture(s) to suture(s) fixation. Further, most knotless anchors are very limited in their utilization, enabling the surgeon to lock in one or two sutures. Larger, screw-in anchors also have other drawbacks in that they are highly dependent on bone quality for fixation. Thus, there is a need for a knotless suture shuttling and anchoring system that relies on an interference fit of the suture itself, which can be utilized in conjunction with traditional anchor points. The knotless suture shuttling and anchoring system disclosed herein satisfies these needs and others as will become apparent to one of ordinary skill after a careful study of the detailed description of the various embodiments.

BRIEF DESCRIPTION OF THE SEVERAL VIEWS OF THE DRAWINGS

The present invention will be more fully understood by reference to the following detailed description of the preferred embodiments of the present invention when read in conjunction with the accompanying drawings, wherein.

Figure 1:
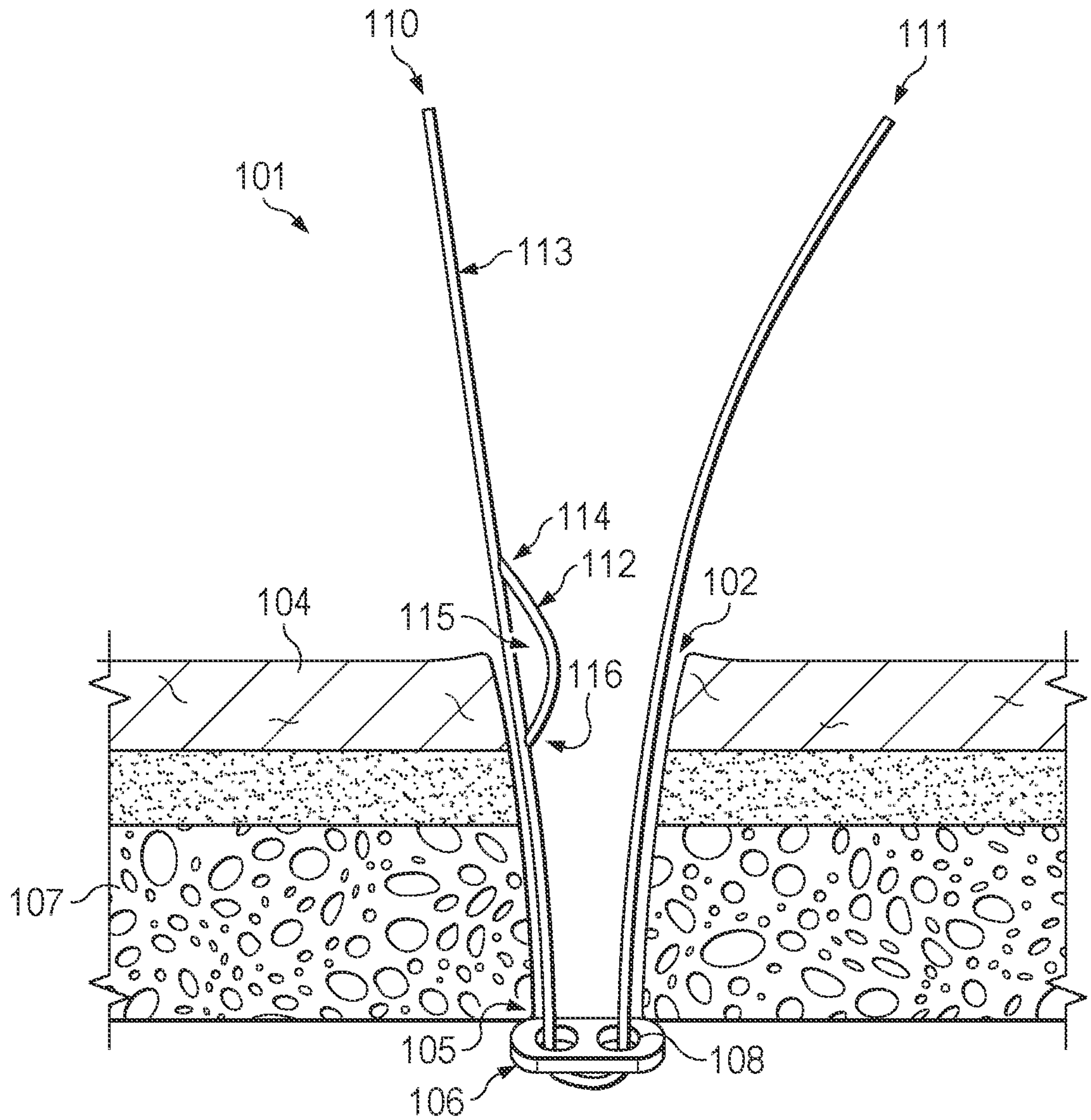
FIG. 1 is a side view of an embodiment of the knotless suture shuttling and anchoring system shown positioned within a cutaway view of a patient's bone and subcutaneous tissue.

The above figures are provided for the purpose of illustration and description only, and are not intended to define the limits of the disclosed invention. Use of the same reference number in multiple figures is intended to designate the same or similar parts. Furthermore, if and when the terms "top," "bottom," "first," "second," "upper," "lower," "height," "width," "length," "end," "side," "horizontal," "vertical," and similar terms are used herein, it should be understood that these terms have reference only to the structure shown in the drawings and are utilized only to facilitate describing the particular embodiment. The extension of the figures with respect to number, position, relationship, and dimensions of the parts to form the preferred embodiment will be explained or will be within the skill of the art after the following teachings of the present invention have been read and understood.

DETAILED DESCRIPTION OF THE INVENTION

Several exemplary embodiments of the disclosed knotless suture shuttling and anchoring system invention(s) will now be described with reference to the drawings. Unless otherwise noted, like elements will be identified by identical numbers throughout all figures. The invention(s) illustratively disclosed herein suitably may be practiced in the absence of any element that is not specifically disclosed herein. The following description is not to be taken in a limiting sense, but is made merely for the purpose of describing the general principles of exemplary embodiments. The scope of the invention(s) should be determined with reference to the claims. Reference throughout this specification to "one embodiment," "an embodiment," or similar language means that a particular feature, structure, or characteristic described in connection with the embodiment is included in at least one embodiment of the inventions disclosed herein. Thus, appearances of the phrases "in one embodiment," "in an embodiment," and similar language throughout this specification may, but do not necessarily, all refer to the same embodiment. Furthermore, the described features, structures, or characteristics of the invention may be combined in any suitable manner in one or more embodiments. In the following description, numerous specific details are provided, such as examples of device structures, methods of use of the devices, etc., to provide a thorough understanding of embodiments of the invention(s). One skilled in the relevant art will recognize, however, that the invention can be practiced without one or more of the specific details, or with other methods, components, materials, and so forth. In other instances, well-known structures, materials, or operations are not shown or described in detail to avoid obscuring aspects of the invention(s).

Knotless suture shuttling and anchoring system, and methods of use thereof, are disclosed herein. It should be noted that while the exemplary embodiments of the invention(s) as described herein are primarily configured for use in the repair of tendons, ligaments, and labrum, the same principles discussed herein could be implemented in connection with other types of surgeries and in conjunction with various other surgical techniques. Indeed, it is contemplated that the knotless suture shuttling and anchoring systems, and methods of use taught herein, could be utilized, without limitation, in any other surgeries requiring fixation. The present invention can be utilized in connection with any fixation within an anchor or implant, including, but not limited to, an all suture anchor, metallic button, or any other type of anchoring device. In addition, the present invention can be utilized to lock, tension, and secure sutures together without having to tie them.

Referring now to FIG. 1, shown is a side view of an embodiment of the knotless suture shuttling and anchoring system shown positioned within a cutaway view of a patient's bone and subcutaneous tissue. In one embodiment, the knotless suture shuttling and anchoring system (101) is a multiple strand suture that may be used in conjunction with an anchor or button (106) (or any other type of anchor point(s) or fixation devices/methods) having one or more eyelets (108) through which one or more suture strands of the system (101) may be passed (as well as other separate fixation sutures as described below). In one embodiment, the knotless suture shuttling and anchoring system and anchor may be delivered through a patient's subcutaneous tissue (104) via an incision (102), and then through a hole (105) punched and/or drilled in the patient's underlying bone (107). It should be noted that the apparent proportions, dimensions, and scale of tissue, bone, anchor, and suture strands have been distorted in FIG. 1 and in the other figures depicted herein to aid in sufficiently depicting and describing the inventions that are being disclosed, but such distortions should in no way be viewed as limiting in any respect.

Still referring to FIG. 1, in one embodiment, the knotless suture shuttling and anchoring system has a primary suture strand (113) with a first tipped suture end (110) and a second opposing suture end (111) that may or not be tipped in various embodiments. Intermediate the first end (110) and second end (111) of the primary strand (113) of the knotless suture shuttling and anchoring system is a secondary suture strand (112) with a first end (114) and second end (116) attached or affixed to the primary strand at different points thereof. The secondary suture strand (112) attached or affixed to the primary suture strand (113) at different points thereof forms a suture loop (115) with a hole that can be utilized to shuttle fixation sutures through the eyelet of the anchor, button, or some other type of fixation device. In one embodiment, the suture loop (115) is formed intermediate or midway between the first tipped suture end and the fixation device. In an alternate embodiment, the suture loop is formed intermediate or approximately midway between the first tipped suture end and the second opposed suture end. In one embodiment, the suture loop is not formed adjacent to either the first tipped suture end or second opposing suture end, but rather somewhere intermediate such ends. In one embodiment, the suture loop is integral to the primary strand such that it is formed as part of the primary strand, not attached or affixed thereto as a separate strand. In such embodiments, the suture loop (115) is an integrated loop formed into the primary suture strand (113). By passing the respective ends of one or more fixation suture(s) through the suture loop, an end of the primary strand may be pulled so as to drag the fixation suture(s) through the anchor eyelet(s). In one embodiment, the suture loop may also be utilized to shuttle the alternate embodiment of the knotless suture shuttling and anchoring system depicted in FIG. 2 through the eyelet until the tapered portion (referred to below as a "locking limb" portion) of such embodiment wedges into an eyelet to create an interference fit, locking the fixation sutures in such eyelet. It should be noted that while the integrated suture loop (115) is depicted as being positioned off-center (not positioned in the middle of the suture) in FIG. 1, alternate embodiments of the knotless suture shuttling and anchoring system may have integrated suture loops positioned in the center or near the center of the overall length of suture, which would facilitate the ability of the knotless suture shuttling and anchoring system to slide the suture loop directionally through a deployed anchor, button, or implant, and would allow the passage of multiple sutures successively. This ability of the knotless suture shuttling and anchoring system provides an advantage over existing sutures having a looped end that will allow only one time passage of sutures in one direction.

Figure 2:
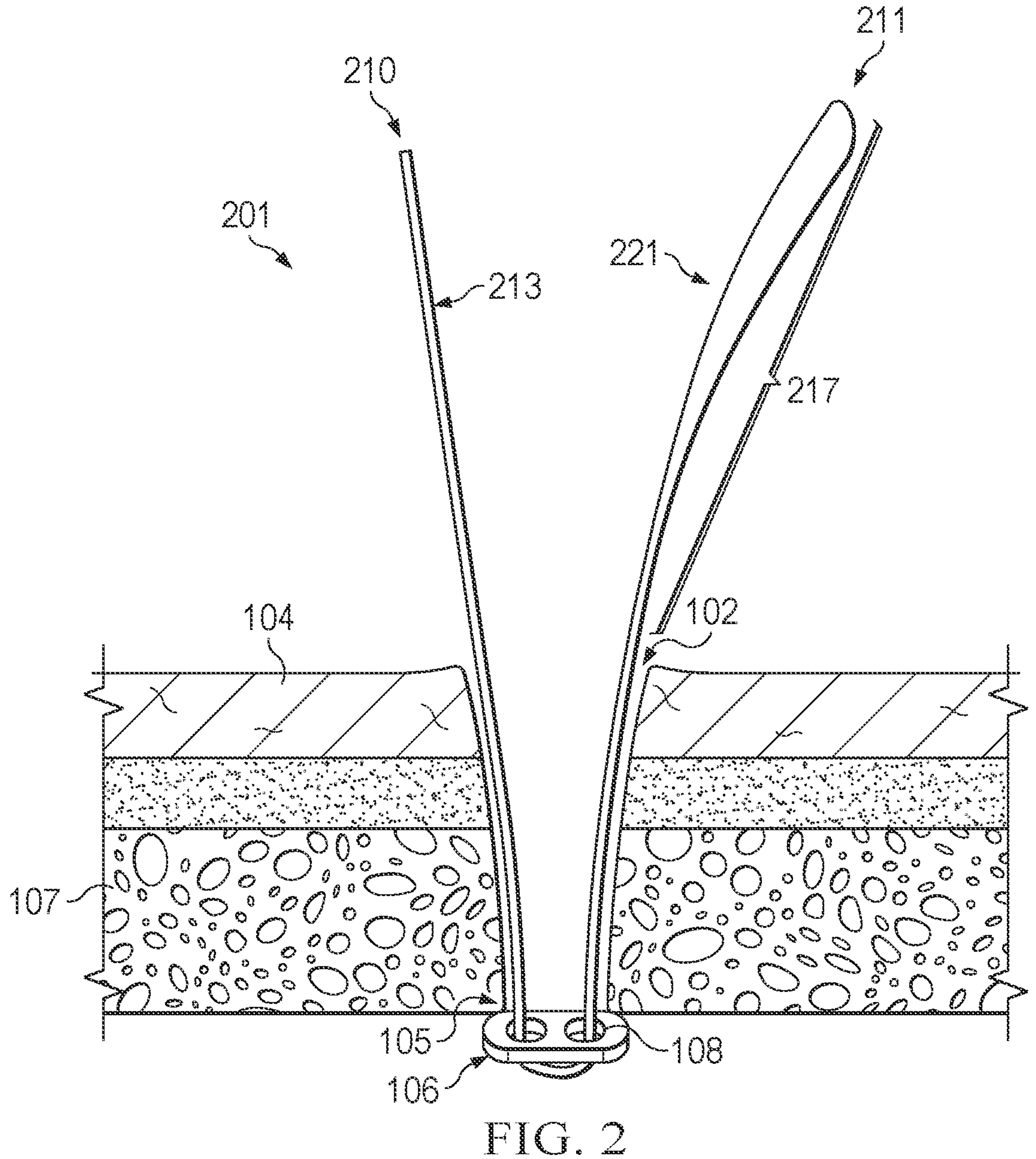
FIG. 2 is a side view of an alternate embodiment of the knotless suture shuttling and anchoring system shown positioned within a cutaway view of a patient's bone and subcutaneous tissue.

Referring now to FIG. 2, shown is a side view of an alternate embodiment of the knotless suture shuttling and anchoring system shown positioned within a cutaway view of a patient's bone and subcutaneous tissue. In the alternate embodiment shown in FIG. 2, the knotless suture shuttling and anchoring system (201) is in some aspects similar to the embodiment of the knotless suture shuttling and anchoring system shown in FIG. 1. The knotless suture shuttling and anchoring system (201) is used in conjunction with an anchor or button (106) (or any other type of fixation device in alternate embodiments) having one or more eyelets (108) through which the strand (213) of the system (201) may be passed. In one embodiment, the knotless suture shuttling and anchoring system (201) and anchor may be deployed through a patient's subcutaneous tissue (104) via an incision point (102), and then through a hole (105) punched and/or drilled in the patient's underlying bone (107). The knotless suture shuttling and anchoring system has a primary suture strand (213) with a first tipped or untipped suture end (210) and a second opposing suture end (211). One noticeable difference between the knotless suture shuttling and anchoring system depicted here at FIG. 2, as compared to the embodiment depicted in FIG. 1, is the presence of a tapered portion (221) of the primary suture, which is referred to herein as a "locking limb" (217) of the knotless suture shuttling and anchoring system (301). Another noticeable difference between the knotless suture shuttling and anchoring system depicted here at FIG. 2, as compared to the embodiment depicted in FIG. 1, is the absence of a suture loop. As described above, the embodiment of the system depicted in FIG. 1 may be utilized to shuttle fixation sutures that have been at least partially inserted into such suture loop, through the anchor eyelet(s). Once the fixation sutures are shuttled through the anchor eyelet(s), the fixation sutures are pulled to the appropriate repair tension. After the appropriate tension is applied to the repair, the first end (210) of the embodiment of the system depicted in FIG. 2 may be pulled to force the tapered locking limb (217) at least partially through the most adjacent anchor eyelet (108). The increasing width/thickness of the locking limb as is passes through the eyelet ultimately wedges such locking limb into the eyelet, creating an interference fit with said eyelet, thereby locking the fixation sutures in the eyelet.

Figure 3:
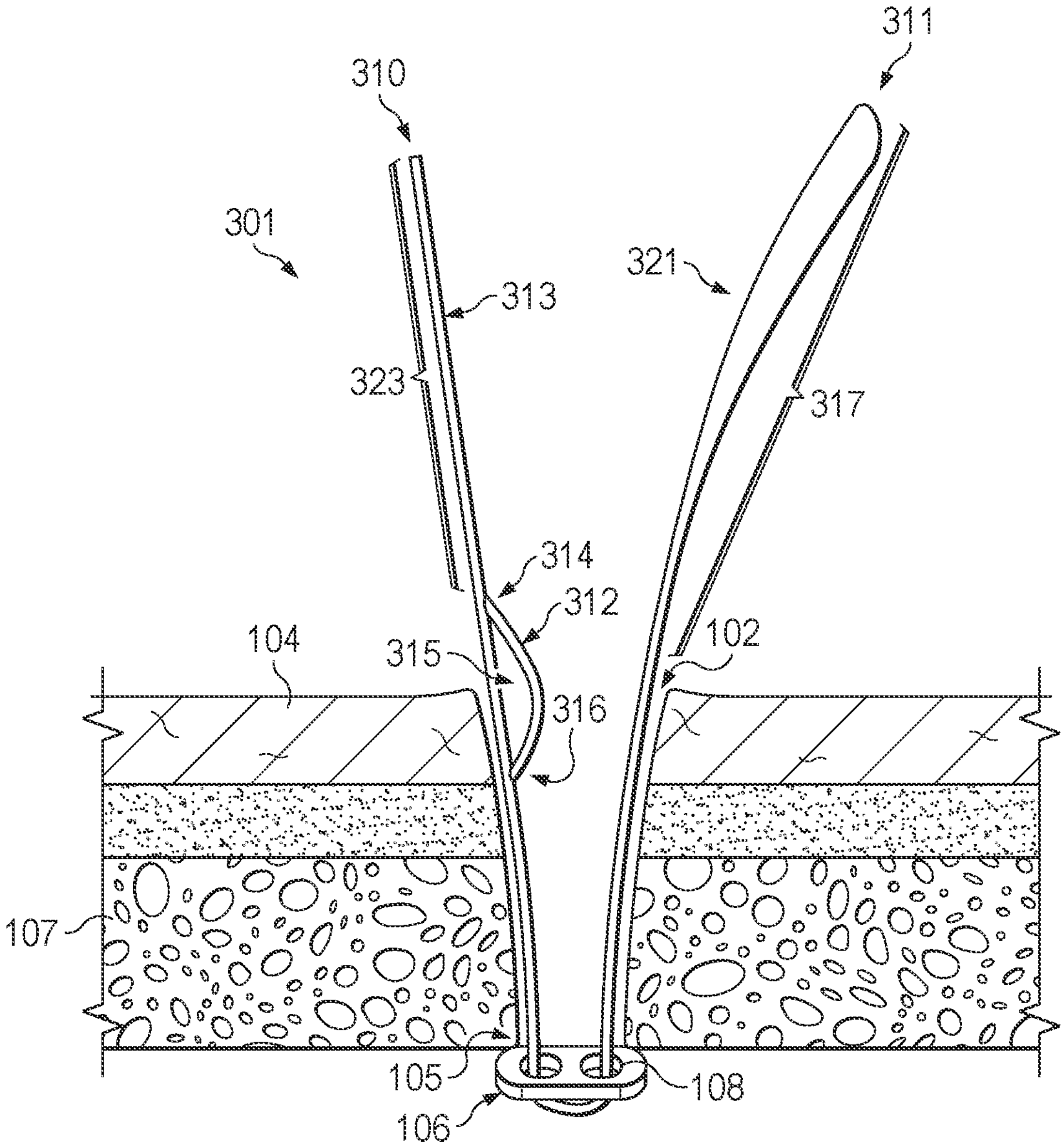
FIG. 3 is a side view of a further alternate embodiment of the knotless suture shuttling and anchoring system shown positioned within a cutaway view of a patient's bone and subcutaneous tissue.

Referring now to FIG. 3, shown is a side view of a further alternate embodiment of the knotless suture shuttling and anchoring system shown positioned within a cutaway view of a patient's bone and subcutaneous tissue. In the alternate embodiment shown in FIG. 3, knotless suture shuttling and anchoring system (301) is in many aspects similar to the embodiment of the knotless suture shuttling and anchoring system shown in FIG. 1. The knotless suture shuttling and anchoring system (301) is a multiple strand suture that may be used in conjunction with an anchor or button (106) having one or more eyelets (108) through which one or more suture strands of the system (301) may be passed (as well as fixation sutures as discussed above). In one embodiment, the knotless suture shuttling and anchoring system (301) and anchor may be delivered through a patient's subcutaneous tissue (104) via an incision point (102), and then through a hole (105) punched and/or drilled in the patient's underlying bone (107). The knotless suture shuttling and anchoring system has a primary suture strand (313) with a first tipped or untipped suture end (310) and a second opposing suture end (311). Intermediate the first end (310) and second end (311) of the primary strand (313) of the knotless suture shuttling and anchoring system is a secondary suture strand (312) with a first end (314) and second end (316) attached or affixed to the primary strand at different points thereof. The secondary suture strand (312) attached or affixed to the primary suture strand (313) at different points thereof forms a suture loop (315) with a hole that can be utilized to shuttle fixation sutures through the eyelet of the anchor, button, or some other type of fixation device. In one embodiment, the suture loop (315) is an integrated loop formed into the primary suture strand (313) as discussed above in connection with the embodiment shown at FIG. 1. By passing the ends of fixation suture(s) through the suture loop, an end of the primary strand may be pulled so as to drag the fixation suture(s) through the anchor eyelet. In one embodiment, the suture loop (115) is formed intermediate or midway between the first tipped suture end and the fixation device. In an alternate embodiment, the suture loop is formed intermediate or approximately midway between the first tipped suture end and the second opposed suture end. In one embodiment, the suture loop is not formed adjacent to either the first tipped suture end or second opposing suture end, but rather somewhere intermediate such ends. It should be noted that while the integrated suture loop (315) is depicted as being positioned off-center (not positioned in the middle of the suture) in FIG. 3, alternate embodiments of the knotless suture shuttling and anchoring system may have integrated suture loops positioned in the center or near the center of the overall length of suture, which would facilitate the ability of the knotless suture shuttling and anchoring system to slide the suture loop directionally through a deployed anchor, button, or implant, and would allow the passage of multiple sutures successively.

Still referring to FIG. 3, in this alternate embodiment, one noticeable difference between the knotless suture shuttling and anchoring system depicted here, as compared to the embodiment depicted in FIG. 1, is the presence of a tapered portion (321) of the primary suture, which is referred to herein as a "locking limb" (317) of the knotless suture shuttling and anchoring system (301). The locking limb may be contrasted with the non-tapered portion of the primary strand, which will be referred to herein as the "shuttling limb" (323), referring to its primary function of shuttling fixation sutures, and even embodiments of the system such as that which is depicted in FIG. 2, to and through the anchor eyelet. In one embodiment of the knotless suture shuttling and anchoring system, the total length of the primary suture, including the locking limb and shuttling portions thereof, is approximately thirty-six inches in length. Further alternate embodiments of the knotless suture shuttling and anchoring system may have a primary suture length that is more or less than thirty-six inches, depending on the surgical application in which it is utilized. In one embodiment of the knotless suture shuttling and anchoring system, the shuttling limb may be composed of a braided polyethylene 2-0 diameter suture, and the tapered locking limb may be composed of a braided polyethylene tape. Other embodiments of the knotless suture shuttling and anchoring system may be composed of a wide variety of materials utilized and having properties optimal for use as sutures in a surgical environment. As described above, the suture loop (315) may be utilized to shuttle fixation sutures that have been at least partially inserted into such suture loop, through the anchor eyelet(s). Once the fixation sutures are shuttled through the anchor eyelet(s), the fixation sutures are pulled to the appropriate repair tension. After the appropriate tension is applied to the repair, the shuttling limb is pulled to shuttle the locking limb at least partially through the most adjacent anchor eyelet. The increasing width/thickness of the locking limb as is passes through the eyelet ultimately wedges such locking limb into the eyelet, creating an interference fit with said eyelet, thereby locking the fixation sutures in the eyelet. It is contemplated that the embodiments of the knotless suture shuttling and anchoring system depicted in FIG. 2 and FIG. 3 could be placed in pairs, inserted into adjacent anchor eyelets from opposite directions, thus creating a bi-directional locking mechanism through the eyelets.

The embodiments of the knotless suture shuttling and anchoring system described herein provide many advantages over prior art fixation methods. Specifically, the system allows for increased flexibility and fixation options. The system can be used in conjunction with various traditional "knotted" anchors, which can be loaded with the knotless suture shuttling and anchoring system, creating a knotless fixation solution. For example, when a surgeon performs a rotator cuff repair, he or she will typically secure sutures from the tendon to the lateral anchor. The knotless suture shuttling and anchoring system described herein will enable a surgeon to load the sutures to the anchor and lock them in place with the tapered locking limb described above. The combination of the knotless suture shuttling and anchoring system described herein having a shuttling limb with integrated loop allows a surgeon to load sutures onto existing anchors with the tapered locking limb suture is used to create an interference fit, locking it into place.

A knotless suture shuttling and anchoring system with an integral loop combined with a tapered suture(s) to create an interference fit would allow for existing traditional anchors to be converted to knotless anchors. This would also allow surgeons to secure suture to suture through a segment of suture, or implant, which would allow the sutures to be tensioned and locked in place. While most knotless anchors are very limited in their utilization, enabling the surgeon to lock in one or two sutures, the knotless suture shuttling and anchoring system described herein will enable a surgeon to lock in many more sutures. Also, while screw-in anchors are highly dependent on bone quality for fixation, the knotless suture shuttling and anchoring system is not highly dependent on bone quality for fixation. Further, utilizing the knotless suture shuttling and anchoring system described herein in conjunction with an existing all suture anchor will enhance the pull out strength of the anchor in addition to locking the sutures in a knotless fashion.

Described herein in one embodiment is a knotless suture shuttling and anchoring system (101) comprising a primary suture strand (113) having a first tipped end (110) and a second opposing end (111), and a secondary suture strand (112) having two opposing ends (114, 116) connected to said primary suture strand to form an integrated suture loop (115), wherein said suture loop is positioned on said primary suture strand intermediate said first tipped end and said second opposing end. The knotless suture shuttling and anchoring system can in one embodiment further comprise a locking limb portion (317) of said primary suture strand, wherein said locking limb portion comprises a portion (321) of said primary suture strand beginning intermediate said suture loop and said second opposing end, tapering in increasing thickness towards said second opposing end. The knotless suture shuttling and anchoring system can in one embodiment further comprise a button or other anchor/fixation device having two eyelets formed thereon, wherein said primary suture strand passes through said two eyelets. In one embodiment, the second opposing end of the primary suture strand of the knotless suture shuttling and anchoring system can be tipped. In one embodiment, the two opposing ends of said second suture strand of the knotless suture shuttling and anchoring system can be affixed to the primary strand. In one embodiment, the two opposing ends of said second suture strand of the knotless suture shuttling and anchoring system can be integrally formed on said primary suture strand. In one embodiment, the suture loop of the knotless suture shuttling and anchoring system is not positioned adjacent to said first tipped end of said primary suture strand. In one embodiment, the suture loop of the knotless suture shuttling and anchoring system is not positioned adjacent to said second opposing end of said primary suture strand.

The inventions described herein may be embodied in other specific forms without departing from the spirit or essential characteristics thereof. The present embodiments are therefore to be considered in all respects as illustrative and not restrictive. Accordingly, the scope of the invention is established by the appended claims rather than by the foregoing description. All changes that come within the meaning and range of equivalency of the claims are embraced therein.

I claim:

1. A knotless suture shuttling and anchoring system comprising:

a primary suture strand having a first tipped end and a second opposing end; and a secondary suture strand having two opposing ends connected to said primary suture strand to form an integrated suture loop; and a locking limb portion of said primary suture strand, wherein said locking limb portion comprises a portion of said primary suture strand beginning at an initial end intermediate said suture loop and said second opposing end, wherein said suture loop is positioned on said primary suture strand intermediate said first tipped end and said second opposing end, wherein said two opposing ends of said secondary suture strand are connected to said primary suture strand at two different points of said primary suture strand, wherein said primary suture strand, together with said secondary suture strand, forms said integrated suture loop, wherein said locking limb portion of said primary suture strand continuously tapers in ever increasing thickness from said initial end to said second opposing end.

2. The knotless suture shuttling and anchoring system of claim 1, further comprising a fixation device having one or more holes formed thereon, wherein said primary suture strand passes through said one or more holes.

3. The knotless suture shuttling and anchoring system of claim 2, wherein said suture loop is not positioned adjacent to said first tipped end of said primary suture strand.

4. The knotless suture shuttling and anchoring system of claim 1, further comprising a button having two eyelets formed thereon, wherein said primary suture strand passes through said two eyelets.

5. The knotless suture shuttling and anchoring system of claim 1, wherein said second opposing end of said primary suture strand is tipped.

6. The knotless suture shuttling and anchoring system of claim 1, wherein said two opposing ends of said second suture strand are affixed to said primary suture strand.

7. The knotless suture shuttling and anchoring system of claim 1, wherein said two opposing ends of said second suture strand are integrally formed on said primary suture strand.

8. The knotless suture shuttling and anchoring system of claim 1, wherein said primary suture strand is at least in part constructed of braided polyethylene.

9. The knotless suture shuttling and anchoring system of claim 2, wherein said locking limb portion of said primary suture strand is at least in part constructed of braided polyethylene tape.

* * * * *